United States Patent
Wu et al.

(10) Patent No.: US 7,522,293 B2
(45) Date of Patent: Apr. 21, 2009

(54) OPTICAL METROLOGY OF MULTIPLE PATTERNED LAYERS

(75) Inventors: Li Wu, Fremont, CA (US); Elina Szeto, San Jose, CA (US); Michael Kwon, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 271 days.

(21) Appl. No.: 11/394,591

(22) Filed: Mar. 30, 2006

(65) Prior Publication Data

US 2007/0229854 A1   Oct. 4, 2007

(51) Int. Cl.
*G01B 11/14* (2006.01)
(52) U.S. Cl. .................................................. 356/625
(58) Field of Classification Search ............... 356/625, 356/630, 600; 702/127
See application file for complete search history.

(56) References Cited

U.S. PATENT DOCUMENTS

| | | | | |
|---|---|---|---|---|
| 6,650,422 | B2* | 11/2003 | Singh et al. | 356/601 |
| 6,785,638 | B2 | 8/2004 | Niu et al. | |
| 6,943,900 | B2 | 9/2005 | Niu et al. | |
| 6,952,271 | B2* | 10/2005 | Niu et al. | 356/625 |
| 2002/0035455 | A1* | 3/2002 | Niu et al. | 703/4 |
| 2004/0017575 | A1* | 1/2004 | Balasubramanian et al. | 356/625 |
| 2004/0233440 | A1* | 11/2004 | Mieher et al. | 356/401 |
| 2004/0267397 | A1 | 12/2004 | Doddi et al. | |
| 2005/0209816 | A1 | 9/2005 | Vuong et al. | |

OTHER PUBLICATIONS

Haykin, S., (1999) *Neural Networks*, Prentice Hall.
Li, L. et al., (Oct. 1997) "New Formulation of the Fourier modal method for crossed surface-relief gratings," *Journal of the Optical Society of America*, 14(10):1024-1035.
Li, L. (May 1996). "Formulation and Comparison of Two Recursive Matrix Algorithms for Modeling Layered Diffraction Gratings," *Journal of the Optical Society of America A* 13(5): 1024-1035.

* cited by examiner

*Primary Examiner*—Tarifur R. Chowdhury
*Assistant Examiner*—Isiaka O Akanbi
(74) *Attorney, Agent, or Firm*—Morrison & Foerster LLP

(57) ABSTRACT

One or more features of multiple patterned layers formed on a semiconductor are determined by obtaining a first measured diffraction signal measured from a first patterned layer before a second patterned layer is formed on top of the first patterned layer. One or more features of the first patterned layer are determined using the first measured diffraction signal. Values of one or more profile parameters of a hypothetical profile of the second patterned layer in combination with the first patterned layer are fixed. A second measured diffraction signal measured from the second patterned layer after the second patterned layer has been formed on top of the first patterned layer is obtained. One or more features of the second patterned layer are determined based on the second measured diffraction signal and the fixed values of the one or more profile parameters.

21 Claims, 6 Drawing Sheets

OPTICAL METROLOGY OF MULTIPLE PATTERNED LAYERS

BACKGROUND

1. Field

The present application generally relates to optical metrology of a structure formed on a semiconductor wafer, and, more particularly, to optical metrology of multiple patterned layers.

2. Description of the Related Art

Optical metrology involves directing an incident beam at a structure, measuring the resulting diffracted beam, and analyzing the diffracted beam to determine a feature of the structure, such as a critical dimension (CD), profile, and the like. In semiconductor manufacturing, optical metrology is typically used for quality assurance. For example, after fabricating a test structure, such as a grating array, in a test pad, in proximity to a corresponding structure in a die, an optical metrology system is used to determine the profile of the test structure. By determining the profile of the test structure, the quality of the fabrication process utilized to form the test structure, and by extension the corresponding structure proximate the test structure, can be evaluated.

When multiple patterned layers are measured using conventional optical metrology, the presence of the bottom patterned layer below the top patterned layer can result in inaccuracy. For example, the presence of the bottom patterned layer can increase the amount of the incident beam that is absorbed, which reduces the strength of the measured diffraction signal. Additionally, the increased number of profile parameters needed to characterize the multiple patterned layers increases the potential for correlated or insensitive profile parameters.

SUMMARY

In one exemplary embodiment, one or more features of multiple patterned layers formed on a semiconductor are determined by obtaining a first measured diffraction signal measured from a first patterned layer before a second patterned layer is formed on top of the first patterned layer. One or more features of the first patterned layer are determined using the first measured diffraction signal. Values of one or more profile parameters of a hypothetical profile of the second patterned layer in combination with the first patterned layer are fixed. A second measured diffraction signal measured from the second patterned layer after the second patterned layer has been formed on top of the first patterned layer is obtained. One or more features of the second patterned layer are determined based on the second measured diffraction signal and the fixed values of the one or more profile parameters.

DESCRIPTION OF THE DRAWING FIGURES

The present application can be best understood by reference to the following description taken in conjunction with the accompanying drawing figures, in which like parts may be referred to by like numerals:

Figures 6A, 6B, 6C:
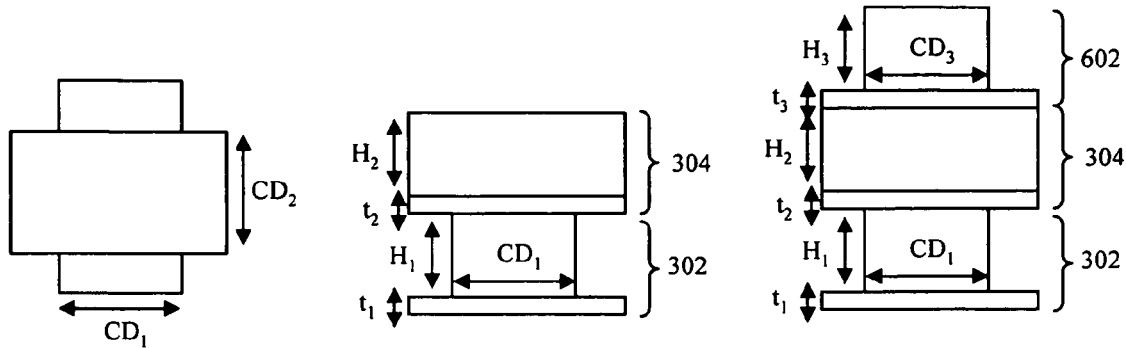
Figure 7:
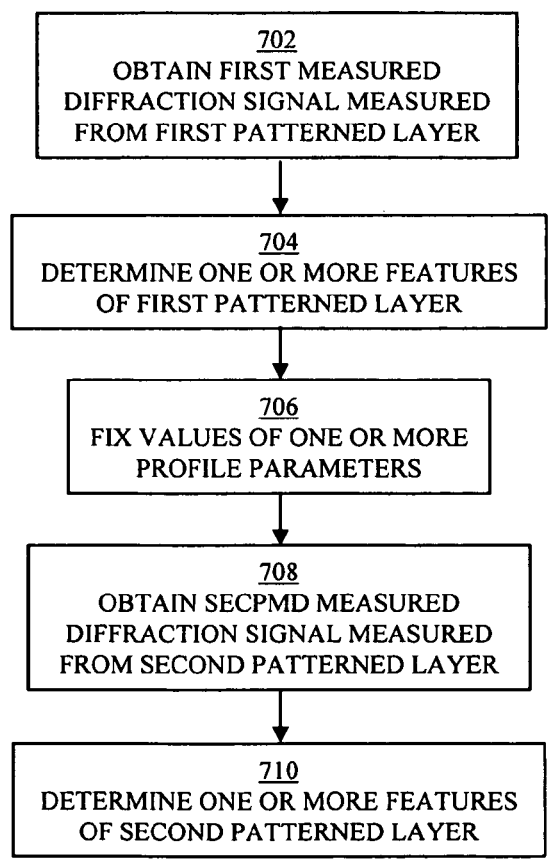
Figure 8:
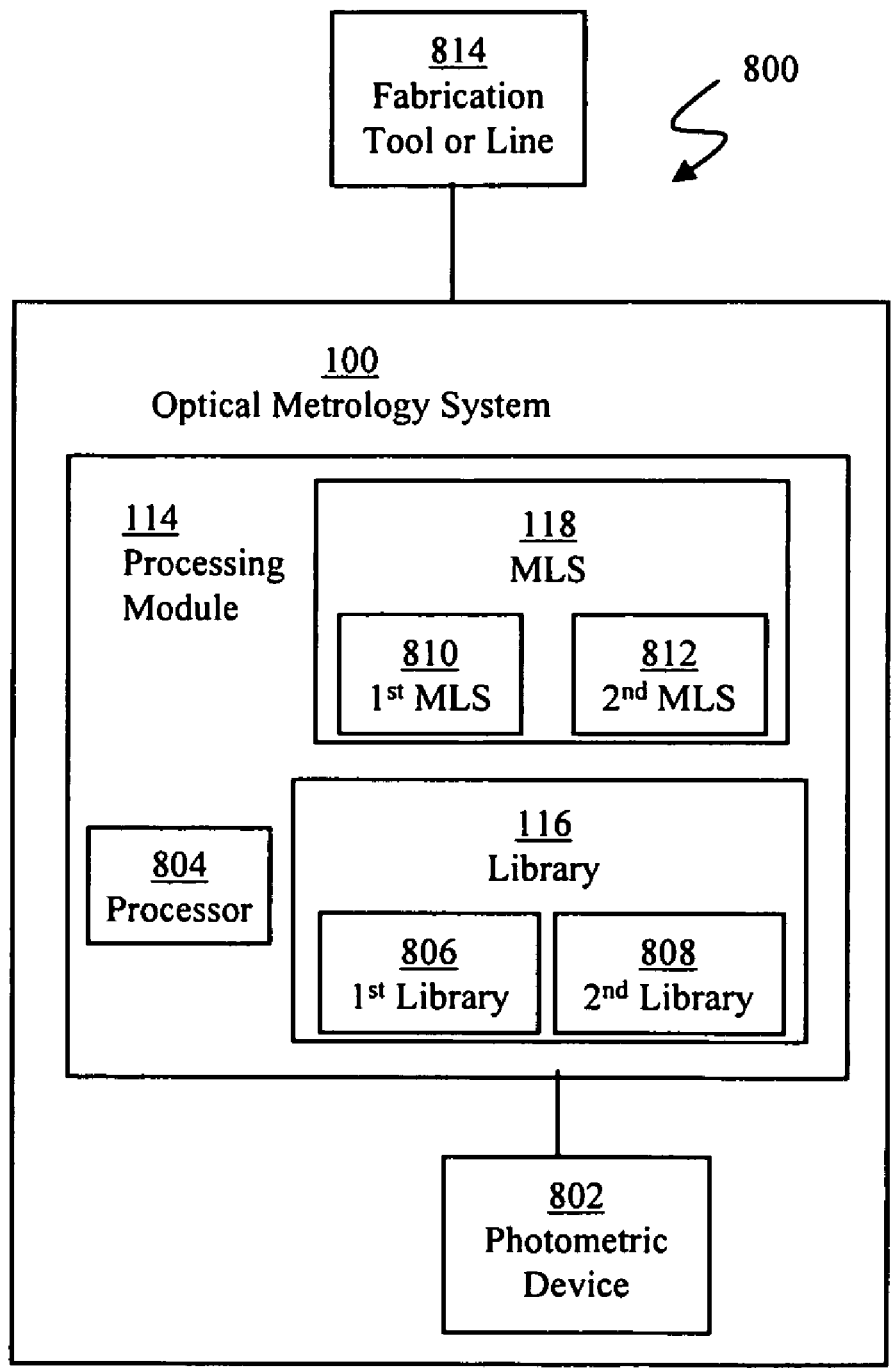

FIGS. 6A, 6B, and 6C depict an exemplary hypothetical profile of multiple patterned layers;

FIG. 7 depicts an exemplary process of determining one or more features of multiple patterned layers; and FIG. 8 depicts an exemplary system configured to determine one or more features of multiple patterned layers.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology

Figure 1:
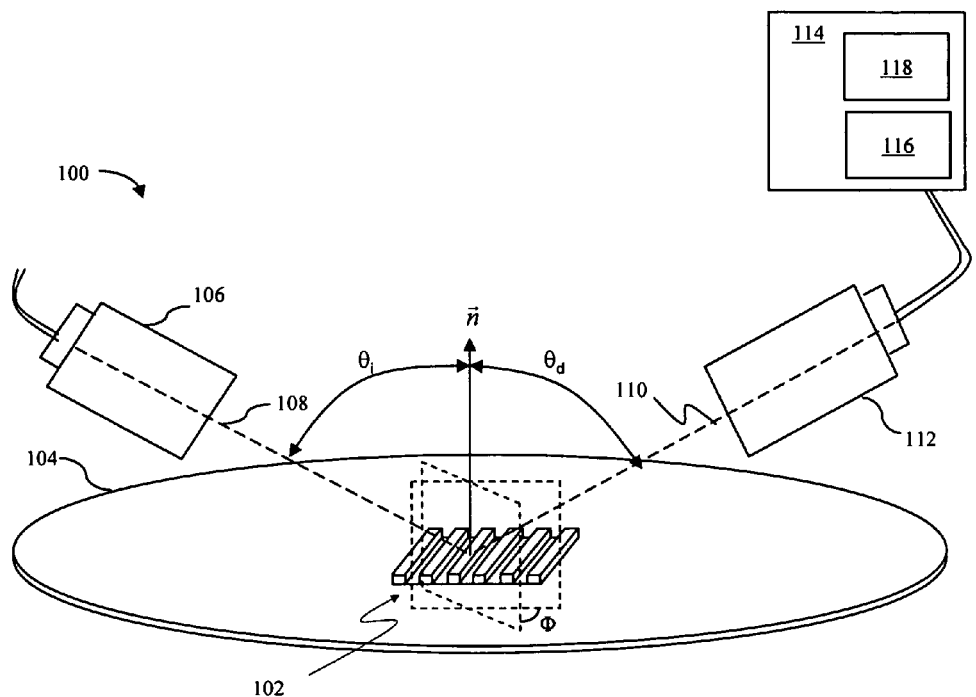
FIG. 1 is an exemplary optical metrology system.

With reference to FIG. 1, an optical metrology system 100 can be used to examine and analyze a structure formed on a semiconductor wafer 104. For example, optical metrology system 100 can be used to determine one or more features of a periodic grating 102 formed on wafer 104, such as a critical dimension, profile, and the like. As described earlier, periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1, optical metrology system 100 can include a photometric device with a source 106 and a detector 112. Periodic grating 102 is illuminated by an incident beam 108 from source 106. The incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, $\tan(\Psi)$, $\cos(\Delta)$, Fourier coefficients, and the like.

Optical metrology system 100 also includes a processing module 114 configured to receive the measured diffraction signal and analyze the measured diffraction signal. As described below, one or more features of periodic grating 102 can then be determined using a library-based process or a regression-based process.

2. Library-Based Process of Determining Feature of Structure

In a library-based process of determining one or more features of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing a hypothetical profile model using a set of profile parameters, then varying the set of profile parameters to generate hypothetical profiles of varying shapes and dimensions. The process of characterizing a profile using a set of profile parameters can be referred to as parameterizing.

Figure 2A:
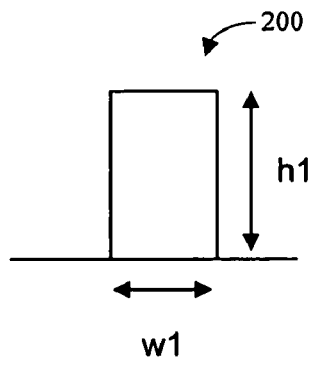
FIGS. 2A-2E depict exemplary hypothetical profiles.
Figure 2C:
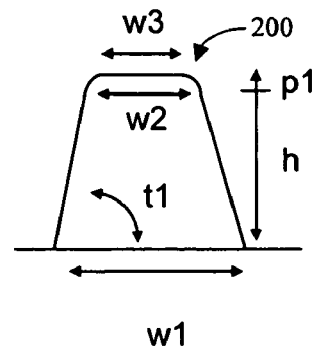
Figure 2B:
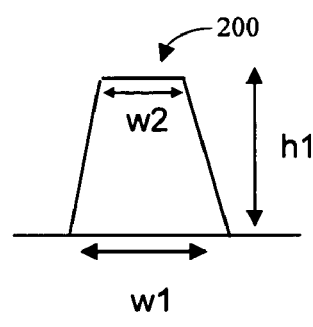
Figure 2D:
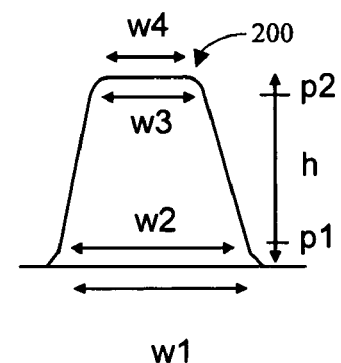
Figure 2E:
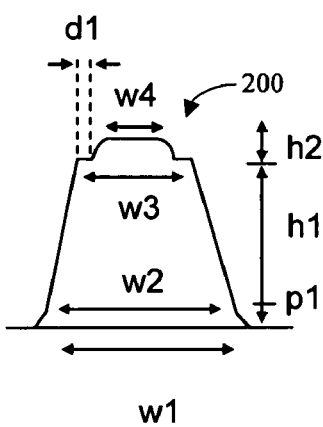

For example, as depicted in FIG. 2A, assume that hypothetical profile 200 can be characterized by profile parameters h1 and w1 that define its height and width, respectively. As depicted in FIGS. 2B to 2E, additional shapes and features of hypothetical profile 200 can be characterized by increasing the number of profile parameters. For example, as depicted in FIG. 2B, hypothetical profile 200 can be characterized by profile parameters h1, w1, and w2 that define its height, bottom width, and top width, respectively. Note that the width of hypothetical profile 200 can be referred to as the critical dimension (CD). For example, in FIG. 2B, profile parameter w1 and w2 can be described as defining the bottom CD and top CD, respectively, of hypothetical profile 200.

As described above, the set of hypothetical profiles stored in library 116 (FIG. 1) can be generated by varying the profile parameters that characterize the hypothetical profile model. For example, with reference to FIG. 2B, by varying profile parameters h1, w1, and w2, hypothetical profiles of varying shapes and dimensions can be generated. Note that one, two, or all three profile parameters can be varied relative to one another.

With reference again to FIG. 1, the number of hypothetical profiles and corresponding simulated diffraction signals in the set of hypothetical profiles and simulated diffraction signals stored in library 116 (i.e., the resolution and/or range of library 116) depends, in part, on the range over which the set of profile parameters and the increment at which the set of profile parameters are varied. The hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

3. Regression-Based Process of Determining Feature of Structure

In a regression-based process of determining one or more features of a structure, the measured diffraction signal is compared to a simulated diffraction signal (i.e., a trial diffraction signal). The simulated diffraction signal is generated prior to the comparison using a set of profile parameters (i.e., trial profile parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of profile parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, the processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. The subsequently generated simulated diffraction signal can be generated using an optimization algorithm, such as global optimization techniques, which includes simulated annealing, and local optimization techniques, which includes steepest descent algorithm.

The simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

4. Rigorous Coupled Wave Analysis

As described above, simulated diffraction signals are generated to be compared to measured diffraction signals. As will be described below the simulated diffraction signals can be generated by applying Maxwell's equations and using a numerical analysis technique to solve Maxwell's equations. It should be noted, however, that various numerical analysis techniques, including variations of RCWA, can be used.

In general, RCWA involves dividing a hypothetical profile into a number of sections, slices, or slabs (hereafter simply referred to as sections). For each section of the hypothetical profile, a system of coupled differential equations generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the hypothetical profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

5. Machine Learning Systems

The simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In one exemplary embodiment, the simulated diffraction signals in a library of diffraction signals, such as library 116 (FIG. 1), used in a library-based process are generated using a MLS. For example, a set of hypothetical profiles can be provided as inputs to the MLS to produce a set of simulated diffraction signals as outputs from the MLS. The set of hypothetical profiles and set of simulated diffraction signals are stored in the library.

In another exemplary embodiment, the simulated diffractions used in regression-based process are generated using a MLS, such as MLS 118 (FIG. 1). For example, an initial hypothetical profile can be provided as an input to the MLS to produce an initial simulated diffraction signal as an output from the MLS. If the initial simulated diffraction signal does not match the measured diffraction signal, another hypothetical profile can be provided as an additional input to the MLS to produce another simulated diffraction signal.

FIG. 1 depicts processing module 114 having both a library 116 and MLS 118. It should be recognized, however, that processing module 114 can have either library 116 or MLS 118 rather than both. For example, if processing module 114 only uses a library-based process, MLS 118 can be omitted. Alternatively, if processing module 114 only uses a regression-based process, library 116 can be omitted. Note, however, a regression-based process can include storing hypothetical profiles and simulated diffraction signals generated during the regression process in a library, such as library 116.

6. Multiple Patterned Layers

Figure 3A:
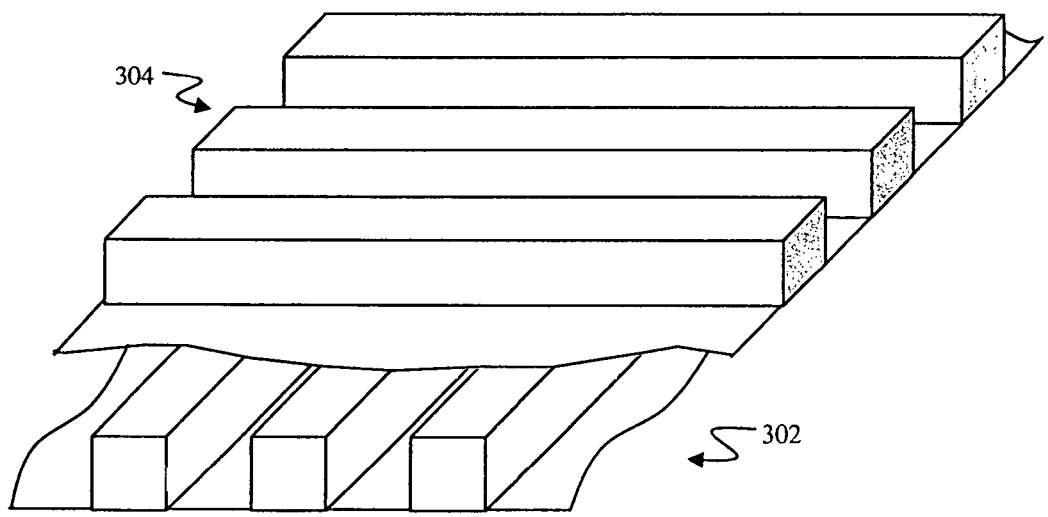
FIG. 3A is a perspective view of exemplary patterned layers, which are subsequent metal layers.
Figure 3B:
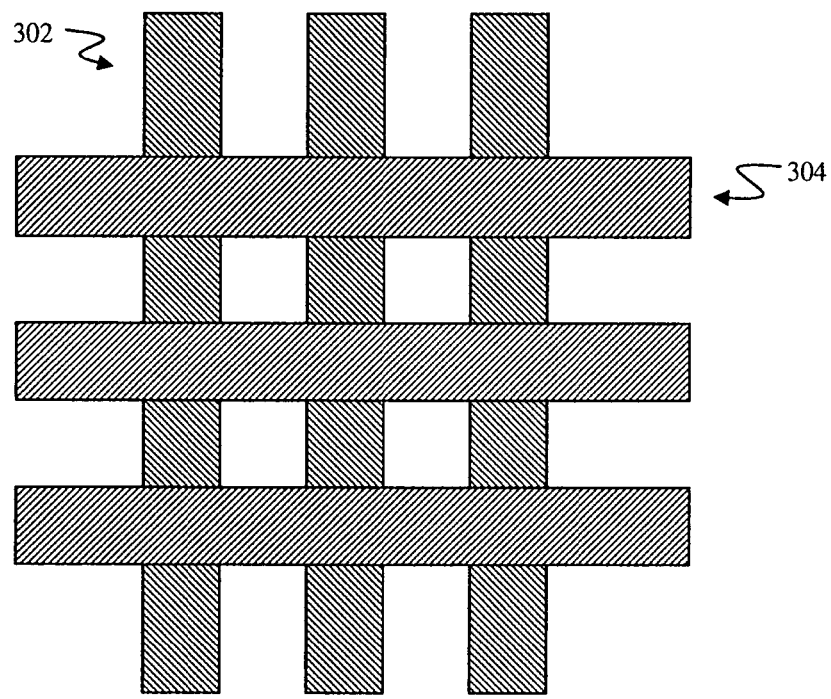
FIG. 3B is a top view of the exemplary patterned layers depicted in FIG. 3A.

FIG. 3A depicts a first patterned layer 302 with a second patterned layer 304 formed on top of first patterned layer 302. In the exemplary embodiment depicted in FIG. 3A, first patterned layer 302 and second patterned layer 304 include metal lines of subsequent metal layers. As depicted in FIG. 3B, metal lines of subsequent metal layers are typically formed to run in different directions. In FIG. 3B, the metal lines in the first patterned layer 302 and the second patterned layer 304 are depicted as running orthogonally. It should be recognized, however, that metal lines of subsequent metal layers can run in various relative angles to each other.

It should be recognized that first patterned layer 302 and second patterned layer 304 can include various types of structures, such as contact holes, posts, islands, and the like. Additionally, it should be recognized that first patterned layer 302 and second patterned layer 304 can have different types of structures (i.e., the first patterned layer 302 can have one type of structure and the second patterned layer 304 can have a different type of structure).

Figure 4:
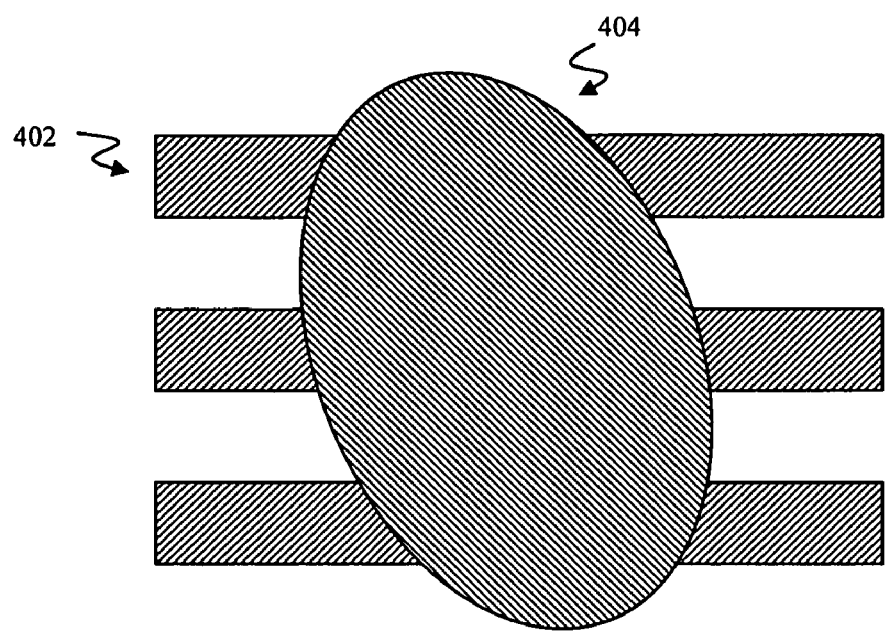
FIG. 4 is a perspective view of exemplary patterned layers, which includes an island formed on top of a metal layer.
Figure 5:
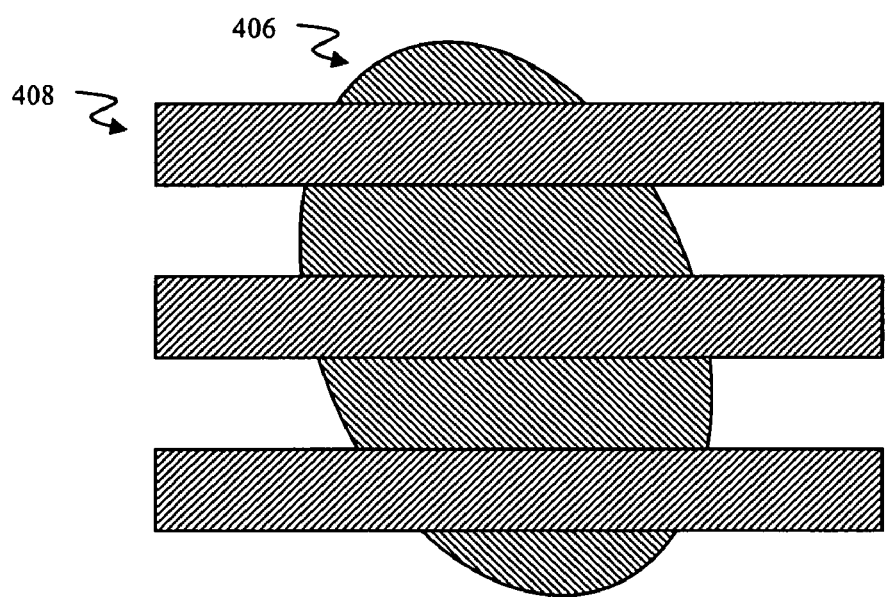
FIG. 5 is a perspective view of exemplary patterned layers, which includes a metal layer formed on top of an island.

For example, FIG. 4 depicts first patterned layer 402, which includes metal lines, and second patterned layer 404, which includes an island formed on top of the metal layer. FIG. 5 depicts first patterned layer 406, which includes an island, and second patterned layer 408, which includes metal lines formed on top of the island.

Furthermore, it should be recognized that any number of structures can be formed in first patterned layer 402 or second patterned layer 404. For example, with reference to FIG. 5, first patterned layer 406 can include two or more islands. It should also be recognized that first patterned layer can include both one-dimensional structures (structures having profiles that vary in only one dimension) and two-dimensional structures (structures having profiles that vary in two dimensions). A metal line is an example of a one-dimensional structure, and an island is an example of a two-dimensional structure.

Although FIGS. 3A, 3B, 4, and 5 depict two patterned layers, it should be recognized that any number of patterned layers can be formed on top of one another. For example, with reference to FIG. 3A, a third patterned layer (not shown), which includes metal lines of a third metal layer, can be formed on top of second patterned layer 304.

7. Optical Metrology of Multiple Patterned Layers

As described above, in conventional optical metrology, when a measured diffraction signal is measured from the second patterned layer 304 to determine a feature of the second patterned layer 304, the presence of the first patterned layer 302 below the second patterned layer 304 can result in inaccuracy. For example, the presence of the first patterned layer 302 can increase the amount of the incident beam that is absorbed, which reduces the strength of the measured diffraction signal. Additionally, the increased number of profile parameters needed to characterize the second patterned layer 304 in combination with the first patterned layer 302 increases the potential for correlated or insensitive profile parameters.

For example, FIGS. 6A and 6B depict an exemplary hypothetical profile of second patterned layer 304 in combination with first patterned layer 302. In the present example, the hypothetical profile includes a top view portion, which is depicted in FIG. 6A, and a cross section view portion, which is depicted in FIG. 6B. As depicted in FIGS. 6A and 6B, profile parameters $CD_1$, $h_1$, and $t_1$ can be defined for the bottom width of the stack, height of the stack, and thickness of the thin layer, respectively, in first patterned layer 302. As also depicted in FIGS. 6A and 6B, profile parameters $CD_2$, $h_2$, and $t_2$ can be defined for the bottom width of the stack, height of the stack, and thickness of the thin film, respectively, in second patterned layer 304. For a detailed description of modeling two-dimensional structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated herein by reference in its entirety.

As noted above, any number of patterned layers can be formed on top of one another. For example, FIG. 6C depicts a third patterned layer 602 formed on top of second patterned layer 304 and first patterned layer 302. As depicted in FIG. 6C, profile parameters $CD_3$, $h_3$, and $t_3$ can be defined for the bottom width of the stack, height of the stack, and thickness of the thin film, respectively, in third patterned layer 602.

FIG. 7 depicts an exemplary process of determining one or more features of multiple patterned layers. For the sake of example, the exemplary process depicted in FIG. 7 will be described in conjunction with first patterned layer 302 (FIGS. 3A and 3B) and second patterned layer 304 (FIGS. 3A and 3B) being subsequent metal layers. As noted above, it should be recognized, however, that first patterned layer 302 (FIGS. 3A and 3B) and second patterned layer 304 (FIGS. 3A and 3B) can include various types of structures.

In the present exemplary embodiment, in step 702, a first measured diffraction signal is obtained. The first measured diffraction signal was measured from a first patterned layer before a second patterned layer is formed on top of the first patterned layer. As described above, the measured diffraction signal can be measured using a photometric device of an optical metrology system. The measured diffraction signal can be obtained directly from the photometric device, or obtained from a buffer, memory, or other storage medium.

In step 704, one or more features of the first patterned layer are determined using the first measured diffraction signal obtained in step 702. As described above, a library-based or regression-based process can be used to determine the one or more features (e.g., CD, profile, and the like) of the first patterned layer using the first measured diffraction signal.

When a library-based process is used, the first measured diffraction signal obtained in step 702 is compared to a library of simulated diffraction signals and corresponding hypothetical profiles of the first patterned layer to determine a closest matching simulated diffraction signal in the library. The one or more features of the first patterned layer are determined based on the hypothetical profile of the first patterned layer in the library corresponding to the closest matching simulated diffraction signal.

When a regression-based process is used, a first simulated diffraction signal is generated using a first hypothetical profile of the first patterned layer. The first measured diffraction signal is to the first simulated diffraction signal. If the first measured diffraction signal and the first simulated diffraction signal match within a matching criterion, one or more features of the first patterned layer are determined based on the first hypothetical profile. If the first measured diffraction signal and the first simulated diffraction signal do not match within the matching criterion, a second simulated diffraction signal is generated using a second hypothetical profile of the first patterned layer, and then the first measured diffraction signal is compared to the second simulated diffraction signal.

In step 706, values of one or more profile parameters of a hypothetical profile of the second patterned layer in combination with the first patterned layer are fixed based on the one or more features of the first patterned layer determined in step 704. In particular, as described above, a library-based or regression-based process can be used to determine one or more features of a structure in optical metrology. As also described above, in both processes, the profile of the structure is characterized using a hypothetical profile defined using a set of profile parameters. In the present exemplary embodiment, one or more of the profile parameters used to define a hypothetical profile of the second patterned layer in combination with the first patterned layer in a library-based or regression-based process are fixed based on the one or more features of the first patterned layer determined in step 704.

In step 708, a second measured diffraction signal is obtained. The second measured diffraction signal was measured from the second patterned layer after the second patterned layer is formed on top of the first patterned layer. The second measured diffraction signal can be measured using a photometric device of an optical metrology system. The second measured diffraction signal can be obtained directly from the photometric device, or obtained from a buffer, memory, or other storage medium. Additionally, the second measured diffraction signal can be measured using the same photometric device used to measure the first measured diffraction signal in step 702.

In step 710, one or more features of the second patterned layer are determined based on the second measured diffraction signal and the fixed values of the one or more profile parameters in step 706. As described above, a library-based or regression-based process can be used to determine the one or more features (e.g., CD, profile, and the like) of the second patterned layer using the second measured diffraction signal and the fixed values of the one or more profile parameters in step 706. In particular, the profile parameters that were not fixed in step 706 can be determined in step 710.

For example, with reference to FIG. 6A, assume that profile parameters $CD_1$, $h_1$, and $t_1$ were determined based on a first measured diffraction signal measured from first patterned layer 302. In this example, profile parameters $CD_2$, $h_2$, and $t_2$ can be determined based on a second measured diffraction signal measured from second patterned layer 304 and the fixed values of profile parameters $CD_1$, $h_1$, and $t_1$.

When a library-based process is used, the second measured diffraction signal obtained in step 708 is compared to a library of simulated diffraction signals and corresponding hypothetical profiles of the second patterned layer in combination with the first patterned layer to determine a closest matching simulated diffraction signal in the library. The second measured diffraction signal obtained in step 708 is compared only to simulated diffraction signals in the library with corresponding hypothetical profiles having one or more profile parameters corresponding to the one or more profiles parameters in step 706 with the same values as fixed in step 706. The one or more features of the second patterned layer are determined based on the hypothetical profile of the second patterned layer in combination with the first patterned layer in the library corresponding to the closest matching simulated diffraction signal.

When a regression-based process is used, a first simulated diffraction signal is generated using a first hypothetical profile of the second patterned layer in combination with the first patterned layer using the values of the one or more profile parameters fixed in step 706. The second measured diffraction signal is compared to the first simulated diffraction signal. If the second measured diffraction signal and the first simulated diffraction signal match within a matching criterion, one or more features of the second patterned layer are determined based on the first hypothetical profile. If the second measured diffraction signal and the first simulated diffraction signal do not match within the matching criterion, a second simulated diffraction signal is generated using a second hypothetical profile of the second patterned layer in combination with the first patterned layer and the values for the one or more profile parameters fixed in step 706, and then the second measured diffraction signal is compared to the second simulated diffraction signal.

As mentioned above, any number of patterned layers can be formed on top of one another. It should be recognized that the exemplary process depicted in FIG. 7 and described above can be extended to apply to more than two patterned layers. In particular, values of the one or more features of the first patterned layer determined in step 704 and the one or more features of the second patterned layer determined in step 710 can be fixed. A third measured diffraction signal can be obtained, where the third measured diffraction signal was measured from the third patterned layer after the third patterned layer is formed on top of the second patterned layer. One or more features of the third patterned layer can then be determined based on the third measured diffraction signal and the fixed values of the one or more features of the first patterned layer determined in step 704 and the one or more features of the second patterned layer determined in step 710.

For example, with reference to FIG. 6C, values of profile parameters $CD_1$, $h_1$, and $t_1$ of first patterned layer 302 and profile parameters $CD_2$, $h_2$, and $t_2$ of second patterned layer 304 can be fixed. A third measured diffraction signal can be obtained of third patterned layer 602. Profile parameters $CD_3$, $h_3$, and $t_3$ can be determined based on the third measured diffraction signal and the fixed values of profile parameters $CD_1$, $h_1$, and $t_1$ of first patterned layer 302 and profile parameters $CD_2$, $h_2$, and $t_2$ of second patterned layer 304.

FIG. 8 depicts an exemplary system 800 configured to determine one or more features of multiple patterned layers. Exemplary system 800 includes optical metrology system 100 with a photometric device 802, which can include source 106 and detector 112 (FIG. 1).

To determine one or more features of multiple patterned layers, photometric device 802 is used to measure a first measured diffraction signal from a first patterned layer before a second patterned layer is formed on top of the first patterned layer. Processor 804 is configured to obtain the first measured diffraction signal measured by photometric device 802. Processor 804 can obtain the first measured diffraction signal directly from photometric device 802 or from a buffer, memory, or other storage medium. Processor 804 is configured to determine one or more features of the first patterned layer using the first measured diffraction signal. Processor 804 is also configured to fix one or more profile parameters of a hypothetical profile of the second patterned layer in combination with the first patterned layer based on the determined one or more features of the first patterned layer.

Photometric device 802 is used to measure a second measured diffraction signal from the second patterned layer after the second patterned layer is formed on top of the first patterned layer. Processor 804 is configured to obtain the second measured diffraction signal measured by photometric device 802. Processor 804 can obtain the second measured diffraction signal directly from photometric device 802 or from a buffer, memory, or other storage medium. Processor 804 is configured to determine one or more features of the second patterned layer based on the second measured diffraction signal and the fixed values of the one or more profile parameters.

As depicted in FIG. 8, in one exemplary embodiment, when a library-based processed is used to determine one or more features of the first patterned layer or the second patterned layer based on the first measured diffraction signal or second measured diffraction signal obtained using photometric device 802, library 116 can include a first library 806 and a second library 808. It should be recognized that first library 806 and second library 808 can be portions of one library or separate libraries.

In the present exemplary embodiment, first library 806 includes sets of hypothetical profiles of the first patterned layer and corresponding simulated diffraction signals. Thus, first library 806 is used in determining one or more features of the first patterned layer based on the first measured diffraction signal measured from the first patterned layer.

Second library 808 includes sets of hypothetical profiles of the second patterned layer in combination with the first patterned layer and corresponding simulated diffraction signals. Thus, second library 808 is used in determining one or more features of the second patterned layer based on the second measured diffraction signal and the fixed values of the one or more profile parameters. In particular, the second measured diffraction signal can be compared only to the simulated diffraction signals in second library 808 with corresponding hypothetical profiles with the fixed values of the one or more profile parameters.

For example, returning to the example described above where a profile parameter corresponding to the bottom CD of the first patterned layer in the combination of the second patterned layer and the first patterned layer is fixed based on the bottom CD determined for the first patterned layer, second library 808 includes sets of hypothetical profiles with the fixed value for the profile parameter corresponding to the bottom CD of the first patterned layer. Second library 808 is used in determining one or more features of the second patterned layer based on the second measured diffraction signal and the fixed one or more profile parameters, such as the profile parameter corresponding to the bottom CD described above.

As also depicted in FIG. 8, in one exemplary embodiment, when a machine learning system (MLS) is used to determine one or more features of a first patterned layer or a second patterned layer based on a first measured diffraction signal or a second measured diffraction signal measured using photometric device 802, MLS 118 can include a first MLS 810 and a second MLS 812. It should be recognized that first MLS 810 and second MLS 812 can be portions of one MLS or separate MLSs.

In the present exemplary embodiment, first MLS 810 is configured to receive hypothetical profiles of the first patterned layer as inputs and provide corresponding simulated diffraction signals as outputs. Thus, first MLS 810 can be used in a regression-based process to determine one or more features of the first patterned layer based on the first measured diffraction signal measured from the first patterned layer.

Second MLS 812 is configured to receive hypothetical profiles of the second patterned layer in combination with the first patterned layer with one or more profile parameters fixed as inputs and provide corresponding simulated diffraction signals as outputs. For example, returning to the example described above where a profile parameter corresponding to the bottom CD of the first patterned layer is fixed based on the bottom CD determined for the first patterned layer, second MLS 812 is configured to receive hypothetical profiles with the fixed value for the profile parameter corresponding to the bottom CD as inputs and generate corresponding simulated diffraction signals as outputs. Second MLS 812 can be used in a regression-based process to determine the one or more features of the second patterned layer.

As noted above, it should be recognized that processing module 114 need not include both library 116 and MLS 118. For example, when only a library-based process is used, MLS 118 can be omitted. Alternatively, when only a regression-based process is used, library 116 can be omitted.

As noted above, any number of patterned layers can be formed on top of one another. Thus, library 116 can include any number of libraries, and MLS 118 can include any number of MLSs. For example, for three patterned layers, library 116 can include three libraries, and MLS 118 can include three MLSs.

As depicted in FIG. 8, exemplary system 800 can be used in conjunction with a fabrication tool or line 814. In particular, the first patterned layer can be formed on a wafer using fabrication tool or line 814. The wafer can then be transported or transferred to exemplary system 800, where photometric device 802 can be used to measure a first measured diffraction signal from the first patterned layer on the wafer. The wafer can then be transported or transferred back to fabrication tool or line 814, where the second patterned layer can be formed on top of the first patterned layer. The wafer can then be transported or transferred back to exemplary system 800, where photometric device 802 can be used to measure a second measured diffraction signal from the second patterned layer on top of the first patterned layer.

Additionally, it should be recognized that exemplary system 800 can be implemented as an in-line system, meaning that exemplary system 800 is integrated with fabrication tool or line 814 to examine and evaluate wafers as the wafers are being processed in fabrication tool or line 814. Alternatively, exemplary system 800 can be implemented as an off-line system, meaning that exemplary system 800 is used to examine and evaluate wafers after they have been processed by fabrication tool or line 814. For example, after being processed on fabrication tool or line 814, wafers can be transported to exemplary system 800 to be examined and evaluated.

Although exemplary embodiments have been described, various modifications can be made without departing from the spirit and/or scope of the present invention. Therefore, the present invention should not be construed as being limited to the specific forms shown in the drawings and described above.

We claim:

1. A method of determining one or more features of multiple patterned layers formed on a semiconductor wafer, the method comprising:
   a) obtaining a first measured diffraction signal measured from a first patterned layer before a second patterned layer is formed on top of the first patterned layer;
   b) determining one or more features of the first patterned layer using the first measured diffraction signal obtained in a);
   c) fixing values of one or more profile parameters of a hypothetical profile of the second patterned layer in combination with the first patterned layer;
   d) obtaining a second measured diffraction signal measured from the second patterned layer after the second patterned layer has been formed on top of the first patterned layer; and
   e) determining one or more features of the second patterned layer based on the second measured diffraction signal and the fixed values of the one or more profile parameters in c).

2. The method of claim 1, wherein the first patterned layer includes a first metal layer, and wherein the second patterned layer includes a second metal layer, wherein the second metal layer runs in a different direction than the first metal layer.

3. The method of claim 2, wherein the second metal layer runs orthogonal to the first metal layer.

4. The method of claim 1, wherein the first patterned layer includes a metal layer, and wherein the second patterned layer includes an island.

5. The method of claim 1, wherein the first and second measured diffraction signals are measured using a photometric device.

6. The method of claim 1, wherein b) comprises:
   comparing the first measured diffraction signal obtained in a) to a library of simulated diffraction signals and corresponding hypothetical profiles of the first patterned layer to determine a closest matching simulated diffraction signal in the library; and
   determining the one or more features of the first patterned layer based on the hypothetical profile of the first patterned layer in the library corresponding to the closest matching simulated diffraction signal.

7. The method of claim 1, wherein b) comprises:
   generating a first simulated diffraction signal using a first hypothetical profile of the first patterned layer;
   comparing the first measured diffraction signal to the first simulated diffraction signal;
   if the first measured diffraction signal and the first simulated diffraction signal match within a matching criterion, determining one or more features of the first patterned layer based on the first hypothetical profile; and
   if the first measured diffraction signal and the first simulated diffraction signal do not match within the matching criterion, generating a second simulated diffraction signal using a second hypothetical profile of the first patterned layer and comparing the first measured diffraction signal to the second simulated diffraction signal.

8. The method of claim 1, wherein e) comprises:
   comparing the second measured diffraction signal obtained in d) to a library of simulated diffraction signals and corresponding hypothetical profiles of the second patterned layer in combination with the first patterned layer to determine a closest matching simulated diffraction signal in the library, wherein the second measured diffraction signal obtained in d) is compared only to simulated diffraction signals in the library with corresponding hypothetical profiles having one or more profile parameters corresponding to the one or more profiles parameters in c) with the same values as fixed in c); and
   determining the one or more features of the second patterned layer based on the hypothetical profile of the second patterned layer in combination with the first patterned layer in the library corresponding to the closest matching simulated diffraction signal.

9. The method of claim 1, wherein e) comprises:
   generating a first simulated diffraction signal using a first hypothetical profile of the second patterned layer in combination with the first patterned layer using the values of the one or more profile parameters fixed in c);
   comparing the second measured diffraction signal to the first simulated diffraction signal;
   if the second measured diffraction signal and the first simulated diffraction signal match within a matching criterion, determining one or more features of the second patterned layer based on the first hypothetical profile; and
   if the second measured diffraction signal and the first simulated diffraction signal do not match within the matching criterion, generating a second simulated diffraction signal using a second hypothetical profile of the second patterned layer in combination with the first patterned layer and the values for the one or more profile parameters fixed in c) and comparing the second measured diffraction signal to the second simulated diffraction signal.

10. The method of claim 1, further comprising:
    f) fixing values of one or more profile parameters of a hypothetical profile of a third patterned layer in combination with the second patterned layer and the first patterned layer;
    d) obtaining a third measured diffraction signal measured from the third patterned layer after the third patterned layer has been formed on top of the second patterned layer; and e) determining one or more features of the third patterned layer based on the third measured diffraction signal and the fixed values of the one or more profile parameters in f).

11. A computer-readable medium containing computer-executable instructions to determine one or more features of multiple patterned layers formed on a semiconductor wafer using optical metrology, comprising instructions for:
   a) obtaining a first measured diffraction signal measured from a first patterned layer before a second patterned layer is formed on top of the first patterned layer;
   b) determining one or more features of the first patterned layer using the first measured diffraction signal obtained in a);
   c) fixing values of one or more profile parameters of a hypothetical profile of the second patterned layer in combination with the first patterned layer;
   d) obtaining a second measured diffraction signal measured from the second patterned layer after the second patterned layer has been formed on top of the first patterned layer; and
   e) determining one or more features of the second patterned layer based on the second measured diffraction signal and the fixed values of the one or more profile parameters in c).

12. The computer-readable medium of claim 11, wherein b) comprises:
   comparing the first measured diffraction signal obtained in a) to a library of simulated diffraction signals and corresponding hypothetical profiles of the first patterned layer to determine a closest matching simulated diffraction signal in the library; and
   determining the one or more features of the first patterned layer based on the hypothetical profile of the first patterned layer in the library corresponding to the closest matching simulated diffraction signal.

13. The computer-readable medium of claim 11, wherein b) comprises:
   generating a first simulated diffraction signal using a first hypothetical profile of the first patterned layer;
   comparing the first measured diffraction signal to the first simulated diffraction signal;
   if the first measured diffraction signal and the first simulated diffraction signal match within a matching criterion, determining one or more features of the first patterned layer based on the first hypothetical profile; and
   if the first measured diffraction signal and the first simulated diffraction signal do not match within the matching criterion, generating a second simulated diffraction signal using a second hypothetical profile of the first patterned layer and comparing the first measured diffraction signal to the second simulated diffraction signal.

14. The computer-readable medium of claim 11, wherein e) comprises:
   comparing the second measured diffraction signal obtained in d) to a library of simulated diffraction signals and corresponding hypothetical profiles of the second patterned layer in combination with the first patterned layer to determine a closest matching simulated diffraction signal in the library, wherein the second measured diffraction signal obtained in d) is compared only to simulated diffraction signals in the library with corresponding hypothetical profiles having one or more profile parameters corresponding to the one or more profiles parameters in c) with the same values as fixed in c); and
   determining the one or more features of the second patterned layer based on the hypothetical profile of the second patterned layer in combination with the first patterned layer in the library corresponding to the closest matching simulated diffraction signal.

15. The computer-readable medium of claim 11, wherein e) comprises:
   generating a first simulated diffraction signal using a first hypothetical profile of the second patterned layer in combination with the first patterned layer using the values of the one or more profile parameters fixed in c);
   comparing the second measured diffraction signal to the first simulated diffraction signal;
   if the second measured diffraction signal and the first simulated diffraction signal match within a matching criterion, determining one or more features of the second patterned layer based on the first hypothetical profile; and
   if the second measured diffraction signal and the first simulated diffraction signal do not match within the matching criterion, generating a second simulated diffraction signal using a second hypothetical profile of the second patterned layer in combination with the first patterned layer and the values for the one or more profile parameters fixed in c) and comparing the second measured diffraction signal to the second simulated diffraction signal.

16. A system configured to determine one or more features of multiple patterned layers formed on a semiconductor wafer using optical metrology, the system comprising:
   a photometric device configured to measure a first measured diffraction signal and a second measured diffraction signal, wherein the first measured diffraction signal is measured from a first patterned layer before a second patterned layer is formed on top of the first patterned layer, and wherein the second measured diffraction signal is measured from the second patterned layer after the second patterned layer has been formed on top of the first patterned layer; and
   a processor configured to:
      a) obtain the first measured diffraction signal;
      b) determine one or more features of the first patterned layer using the first measured diffraction signal obtained in a);
      c) fix values of one or more profile parameters of a hypothetical profile of the second patterned layer in combination with the first patterned layer;
      d) obtain the second measured diffraction signal; and
      e) determine one or more features of the second patterned layer based on the second measured diffraction signal and the fixed values of the one or more profile parameters in c).

17. The system of claim 16, further comprising:
   a first library of simulated diffraction signals and corresponding hypothetical profiles of the first patterned layer, and
   wherein the processor is configured to:
      compare the first measured diffraction signal to the first library to determine a closest matching simulated diffraction signal in the first library; and
      determine the one or more features of the first patterned layer based on the hypothetical profile of the first patterned layer in the first library corresponding to the closest matching simulated diffraction signal.

18. The system of claim 16, further comprising:
   a first machine learning system configured to generate simulated diffraction signals using hypothetical profiles of the first patterned layer as inputs, and
   wherein the processor is configured to:

compare the first measured diffraction signal to a first simulated diffraction signal generated by the first machine learning system;

if the first measured diffraction signal and the first simulated diffraction signal match within a matching criterion, determine one or more features of the first patterned layer based on a first hypothetical profile used to generate the first simulated diffraction signal; and if the first measured diffraction signal and the first simulated diffraction signal do not match within the matching criterion, compare the first measured diffraction signal to a second simulated diffraction signal generated by the first the machine learning system using a second hypothetical profile of the first patterned layer as input.

19. The system of claim 16, further comprising:

a second library of simulated diffraction signals and corresponding hypothetical profiles of the second patterned layer in combination with the first patterned layer, and wherein the processor is configured to:

compare the second measured diffraction signal to the second library to determine a closest matching simulated diffraction signal in the second library, wherein the second measured diffraction signal is compared only to simulated diffraction signals in the second library with corresponding hypothetical profiles having one or more profile parameters corresponding to the one or more profiles parameters in c) with the same values as fixed in c); and determine the one or more features of the second patterned layer structure based on the hypothetical profile of the second patterned layer in combination with the first patterned layer in the second library corresponding to the closest matching simulated diffraction signal.

20. The system of claim 16, further comprising:

a second machine learning system configured to generate simulated diffraction signals using hypothetical profiles of the second patterned layer in combination with the first patterned layer using the values of the fixed one or more profile parameters as inputs, and wherein the processor is configured to:

compare the second measured diffraction signal to a first simulated diffraction signal generated by the second machine learning system;

if the second measured diffraction signal and the first simulated diffraction signal match within a matching criterion, determine one or more features of the second patterned layer based on a first hypothetical profile used to generate the first simulated diffraction signal; and if the second measured diffraction signal and the first simulated diffraction signal do not match within the matching criterion, compare the second measured diffraction signal to a second simulated diffraction signal generated by the second machine learning system using a second hypothetical profile of the second patterned layer in combination with the first patterned layer as input.

21. The system of claim 16, further comprising:

a fabrication tool or line, wherein the first patterned layer is formed on the wafer using the fabrication tool or line, and wherein the second patterned layer is formed on top of the first patterned layer using the fabrication tool or line.

* * * * *